United States Patent [19]

Bühring

[11] Patent Number: 5,741,917
[45] Date of Patent: Apr. 21, 1998

[54] PROCESS FOR THE PREPARATION OF ACYLOXYALKANESULFONATES HAVING IMPROVED PROPERTIES

[75] Inventor: Dirk Bühring, Suzano, Brazil

[73] Assignee: Hoechst Aktiengesellschaft, Frankfurt, Germany

[21] Appl. No.: 624,905

[22] Filed: Mar. 27, 1996

[30] Foreign Application Priority Data

Mar. 29, 1995 [DE] Germany ............... 195 11 460.4

[51] Int. Cl.$^6$ ...................................... C11D 1/28
[52] U.S. Cl. ........................ 554/92; 554/88; 554/97
[58] Field of Search .................................. 559/85

[56] References Cited

U.S. PATENT DOCUMENTS 5,384,421  1/1995  Day et al. ................... 554/92

*Primary Examiner*—Gary Geist
*Assistant Examiner*—Deborah D. Carr
*Attorney, Agent, or Firm*—Connolly and Hutz

[57] ABSTRACT

Process for the preparation of acyloxyalkanesulfonates having improved properties The acyloxyalkanesulfonates are prepared according to the invention by esterification of branched fatty acids with hydroxyalkanesulfonates. Because of the specific fatty acid, the use of a consistency regulator is not required. Highly concentrated acyloxyalkanesulfonates are obtained which, as a further advantageous property, have good water solubility.

9 Claims, No Drawings

PROCESS FOR THE PREPARATION OF ACYLOXYALKANESULFONATES HAVING IMPROVED PROPERTIES

The invention relates to a process for the preparation of acyloxyalkanesulfonates having improved properties by esterification of fatty acids with hydroxyalkane-sulfonates.

Acyloxyalkanesulfonates are valuable anionic surfactants which are chiefly used for the preparation of Syndet soaps, cosmetic compositions and cleaning formulations. They are advantageously prepared by esterification of at least one fatty acid with at least one hydroxyalkane-sulfonate (direct esterification). Such a process is described, for example, in EP-A-0 585 071 (U.S. Pat. No. 5,384,421). In this process, the fatty acid and the salt of the hydroxyalkanesulfonic acid are reacted in the presence of an esterification catalyst and a consistency regulator at a temperature of 180° to 240° C. with simultaneous removal of water present. The consistency regulators used are certain paraffins. The use of such compounds is necessary, because the reaction mixture becomes highly viscous with advancing esterification. Although a lower viscosity of the reaction mixture is achieved with consistency regulators and the reaction is facilitated, the esterification product contains the compounds used, as a result of which the sought-after acyloxyalkane-sulfonate is obtained diluted to a greater or lesser extent.

It has now surprisingly been found that the direct esterification in question can be carried out without consistency regulator and thus an esterification product having a high content of acyloxyalkanesulfonate is obtained, if the fatty acids used are those having a branched (non-straight-chain) hydrocarbon radical. It is an unexpected result, that the reaction of hydroxyalkane-sulfonates precisely with branched fatty acids can be carried out without a consistency regulator. It is possible to prepare in this manner highly concentrated acyloxyalkanesulfonates which, as further unexpected properties, have good water solubility, high foaming capacity and good hard water stability.

The process of the invention for the preparation of acyloxyalkanesulfonates having improved properties by esterification of fatty acids with hydroxyalkane-sulfonates comprises esterifying at least one fatty acid of the formula 1 RCOOH (1), in which R is a branched hydrocarbon radical having 5 to 31 carbon atoms, or a mixture of branched and unbranched hydrocarbon radicals each having 5 to 31 carbon atoms, the amount of unbranched radicals being at most 50% by weight, with at least one hydroxyalkanesulfonate of the formula 2 HO—$R^1$—$SO_3$X (2), in which $R^1$ is a $C_2$ to $C_4$-alkylene or a divalent di-$C_2$ to $C_4$-alkyl ether radical and X is an alkali metal or ammonium, in the presence of an esterification catalyst and in the absence of a consistency regulator at a temperature of 180° to 250° C. with removal of the water present, a product having a high content of acyloxyalkanesulfonate being obtained.

In the process of the invention, therefore, selected fatty acids are used, that is those having a saturated or unsaturated, branched hydrocarbon radical having (in total) 5 to 31 carbon atoms. The hydrocarbon radical can have one or more branches, generally it contains only one branch, that is in the a-position to the carboxyl group. The branch or branches themselves can be short or long, unbranched or branched, preferably unbranched, saturated or unsaturated, preferably saturated. The branched hydrocarbon radical R in formula 1 is preferably a radical of the formula 1a below

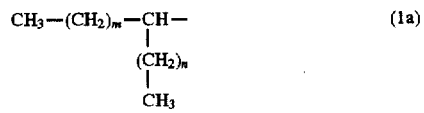

in which m is an integer from 4 to 18, preferably 4 to 14, and n is 0 or an integer from 1 to 10, preferably 0 or an integer from 1 to 6. The fatty acids preferred according to the invention therefore correspond to the formula 1b below

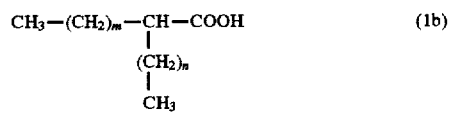

in which m and n have the specified meanings. The branched (non-straight-chain) fatty acids to be used according to the invention are known and are commercially available. Branched carboxylic acids can be prepared, for example, from inner olefins, by converting these to the aldehyde by oxo synthesis and oxidizing the aldehyde compounds to the carboxylic acid. Examples of suitable branched fatty acids are: 2-ethylhexanoic acid, 2-pentyl-octanoic acid, 2-butylnonanoic acid, 2-propyldecanoic acid, 2-ethylundecanoic acid, 2-butylundecanoic acid, 2-methyldodecanoic acid, 2-ethyltridecanoic acid and 2-methyltetradecanoic acid and mixtures thereof.

According to the invention, mixtures of at least one branched fatty acid and at least one unbranched (straight-chain) fatty acid can also be used, the content of unbranched fatty acids being at most 50% by weight, percentages by weight based on the mixture. Just as with the branched fatty acids, the unbranched can also be saturated or unsaturated. In the case of unbranched fatty acids, the radical R is preferably $C_5$ to $C_{21}$-alkyl or $C_5$ to $C_{21}$-alkenyl or a mixture thereof. The alkenyl radicals are preferably monounsaturated to triunsaturated. Examples of unbranched fatty acids which may be mentioned are caproic acid, capric acid, lauric acid, myristic acid, stearic acid, arachic acid, oleic acid, linoleic acid, linolenic acid, coconut fatty acid and tallow fatty acid.

The hydroxyalkanesulfonate which is reacted with the branched fatty acid or with said mixture of branched and unbranched fatty acids is not critical. Preferred salts of hydroxyalkanesulfonic acids are those of the formula 2, in which $R^1$ is —$CH_2CH_2$—, —$(CH_2)_3$—, —$CH_2CH(CH_3)$— or —$CH_2CH_2OCH_2CH_2$—, ethylene being particularly preferred, and the counterion X is $NH_4$ or an alkali metal, preferably sodium or potassium. The hydroxyalkanesulfonate particularly preferred according to the invention is potassium or sodium isethionate. The hydroxyalkanesulfonic acid salts can be used as such; preferably they are used in the form of an aqueous solution, generally as a 40 to 65% strength by weight solution.

The reaction according to the invention of fatty acid and hydroxyalkanesulfonate is carried out in the presence of a catalyst. Suitable esterification catalysts are described extensively in said EP-A-0 585 071 which is incorporated herein by reference. These are alkane-sulfonic acids, hydroxyalkanesulfonic acids, arylsulfonic acids, inorganic acids such as sulfuric acid, phosphoric acid, phosphorous acid, boric acid or anhydrides thereof, heavy metal salts such as zinc sulfate, zirconium sulfate, zinc isethionate, zinc borate, aluminum sulfate, titanium sulfate or tungsten phosphate, metal oxides such as zinc oxide, aluminum oxide, magnesium oxide, cerium oxide, zirconium oxide or lanthanum oxide, in addition mixtures of two or more of said catalysts, and soaps which are formed from heavy metals and metal oxides. A particularly preferred esterification catalyst is zinc oxide. The esterification catalyst is used in an amount of generally 0.05 to 2% by weight, preferably 0.05 to 1% by weight, percentages by weight based on fatty acid and hydroxyalkanesulfonic acid salt.

The reaction of fatty acid and hydroxyalkanesulfonic acid salt, generally in a molar ratio of 1:1 to 2:1, preferably about 1:1, is carried out according to the invention at a temperature of 180° to 250° C. The preferred temperature range is 200° to 240° C. The water possibly introduced into the reaction mixture with the starting components and the water formed by the esterification reaction is continuously discharged from the reaction mixture. The reaction mixture, because of the specific fatty acid used, is homogeneous until the end of the reaction, even at 100% conversion, is of relatively low viscosity and readily stirrable; a consistency regulator is not required. The time up to the sought-after degree of conversion of fatty acid or hydroxyalkanesulfonate is about 4 to 8 hours. Generally, for example for reasons of time, 100% conversion is not sought after, but the esterification reaction is interrupted at a lower percentage, for example at 75 to 90% by weight of acyloxyalkanesulfonate.

The process of the invention can, in detail, be carried out, for example, in such a manner that—at atmospheric pressure—the fatty acid, the salt of the hydroxyalkanesulfonic acid and the esterification catalyst are introduced into a reaction vessel and the mixture is heated to the specified temperature with stirring. Water present continuously distills off as early as during the heating of the reaction mixture and then further during the running esterification reaction. The process of the invention can also be carried out by the method described in EP-A-0 585 071. Here, the esterification reaction is carried out partly at atmospheric pressure and partly under application of a vacuum for more rapid discharge of the water. After the sought-after degree of conversion has been achieved, the esterification reaction is terminated, for example by cooling. The reaction product obtained is liquid or solid at room temperature. The product solid at room temperature can be formulated, for example, using a flaking roller or a cooling belt.

By means of the process of the invention, which can also be carried out industrially, concentrated acyloxyalkanesulfonates can be prepared. As further advantageous properties, they have good water solubility, strong foam formation and good hard water stability and a beneficially acting skin feel. The products obtained according to the invention are therefore also especially suitable for aqueous formulations. Owing to the direct esterification (direct condensation) the use of fatty acid chlorides can be dispensed with, which would otherwise have to be prepared from fatty acid in a separate step. The use of consistency regulators and/or diluents, which generally do not represent valuable materials in, for example, cleaning formulations and cosmetic compositions, is not necessary. In the process of the invention, the reaction mixture therefore essentially comprises only branched fatty acid, hydroxyalkanesulfonate and esterification catalyst.

The solid or liquid reaction product generally contains, as mentioned above, 75 to 90% by weight of acyloxyalkanesulfonate, based on the solid or liquid total product. The salts of acyloxyalkanesulfonic acids obtained according to the invention correspond to the formula 3 below

(3)

in which R, $R^1$ and X have the specified meanings.

The invention is now described in still more detail with reference to examples. Percentages are by weight, unless stated otherwise.

EXAMPLE 1

639 g (3 mol) of isotridecanoic acid having a mean molecular weight of 214 (see below for composition in detail), 775 g of an aqueous 57% strength sodium isethionate solution (that is 3 mol of sodium isethionate) and 3.0 g of zinc oxide are introduced into a 2 l reaction vessel with ground glass joints equipped with anchor agitator, descending distillation bridge, internal thermometer and nitrogen inlet. The mixture is heated to 235° C. and kept at this temperature. The water introduced into the mixture and formed in the direct condensation distills off continuously. The reaction is interrupted at a sodium isotridecanoylisethionate content of 79%. The reaction product is cooled to 120° C. and poured onto a metal sheet for cooling. It essentially consists of 79% of sodium isotridecanoylisethionate (Epton titration), 10% of lauric acid (potentiometric titration) and 11% of sodium isethionate (calculated from the conversion rate).

Composition of the isotridecanoic acid (main constituents):

19% 2-pentyloctanoic acid, 18% 2-butylnonanoic acid,

17% 2-propyldecanoic acid, 17% 2-ethylundecanoic acid,

25% 2-methyldodecanoic acid, 3% n-tridecanoic acid.

EXAMPLE 2

554 g (2.6 mol) of isotridecanoic acid (composition as in Example 1), 517 g of an aqueous 57% strength sodium isethionate solution (2 mol of sodium isethionate) and 2.0 g of zinc oxide are introduced into the apparatus of Example 1. The batch is heated to 235° C. and kept at this temperature, water present distilling off continuously. At a sodium isotridecanoylisethionate content of 77%, vacuum (0.5 mbar) is applied, and at a temperature of still 235° C., 97 g of the isotridecanoic acid used in excess are distilled off. The product is cooled to 150° C. and poured onto a metal sheet for cooling. The end product comprises 89% of sodium isotridecanoylisethionate (Epton titration); the acid number is 19 mg of KOH/g (potentiometric titration).

EXAMPLE 3

391 g (1.8 mol) of isotridecanoic acid (composition as in Example 1), 353 g (1.8 mol) of sodium 2-(2-hydroxyethoxy)ethanesulfonate and 2.0 g of zinc oxide are introduced into the apparatus of Example 1. The batch is heated to 235° C. and kept at this temperature. The water formed in the direct condensation distills off continuously. The reaction is interrupted at a sodium 2-(2-isotridecanoyloxyethoxy)ethanesulfonate content of 82% and the product is poured onto a metal sheet for cooling. The reaction product essentially consists of 82% sodium 2-(2-isotridecanoyloxyethoxy)ethanesulfonate (Epton titration), 6% isotridecanoic acid (potentiometric titration) and 12% sodium 2-(2-hydroxyethoxy)ethane-sulfonate (calculated from the conversion rate).

EXAMPLE 4

561 g (2.5 mol) of $C_{13}$ to $C_{15}$-carboxylic acid having a mean molecular weight of 228 (see below for composition in detail), 511 g of an aqueous 57% strength sodium isethionate solution (2 mol of sodium isethionate) and 1.6 g of zinc oxide are introduced into the apparatus of Example 1. The mixture is heated to 220° C. and kept at this temperature. The water introduced into the mixture and formed in the direct condensation distills off continuously. At a product content of 77%, vacuum (0.5 mbar) is applied, and at a temperature of still 220° C., 97 g of the carboxylic acid used in excess are distilled off. The reaction product is poured onto a metal sheet for cooling. It comprises 89% of sodium $C_{13}$ to $C_{15}$-acylisethionate (Epton titration); the acid number is 10 mg of KOH/g (potentiometric titration).

Composition of the $C_{13}$ to $C_{15}$-carboxylic acid (main constituents present at an amount of >1%):

1.3% 2-propyldecanoic acid, 3.2% 2-ethylundecanoic acid, 19.3% 2-methyldodecanoic acid, 34.2% n-tridecanoic acid, 1.4% 2-butylundecanoic acid, 2.6% 2-ethyltridecanoic acid, 12.5% 2-methyltetradecanoic acid, 10.6% n-pentadecanoic acid.

Test of water solubility and foam formation:

1. The products according to the invention of the Examples 1 to 4 and a product of the prior art, that is sodium cocoylisethionate containing 66% of surfactant and about 28% of free fatty acid (comparison), are tested for water solubility, by studying at up to which maximum concentration in deionized water at 20° C. a clear solution is obtained. The values are summarized in Table 1 below:

TABLE 1

| Water solubility (clear solutions, 20° C., deionized water) | | | | |
|---|---|---|---|---|
| Comparison | Example 1 | Example 2 | Example 3 | Example 4 |
| <1% | 20% | 30% | 30% | 10% |

It is shown that, with the comparison product, a clear solution is only obtained if the amount of product is below 1%, whereas with the products according to the invention concentrations of up to 30% are possible, percentages based on the solution.

2. The products according to the invention of the Examples 1 to 3 and two products of the prior art, that is sodium cocoylisethionate containing 66% of surfactant and about 28% of free fatty acid (comparison 1) and sodium cocoylisethionate containing >90% of surfactant and <5% of free fatty acid (comparison 2) are tested for Ross/Miles foam in water having 15 German hardness degrees (150 dH), 37° C. and pH 7 at product concentrations of 1% and 0.03% in each case (percentages based on the aqueous solution). The values of the initial foam height (that is the foam height immediately after discharging the solution) and the foam height after 5 minutes, in mm, are summarized in Table 2 below:

TABLE 2

| Ross/Miles foam, pH 7, 15° dH, 37° C.: initial foam height and foam height after 5 minutes, in mm | | | | | |
|---|---|---|---|---|---|
| Active substance content | Comparison 1 | Comparison 2 | Example 1 | Example 2 | Example 3 |
| 1% | 270/250 | 270/240 | 270/260 | 270/270 | 270/260 |
| 0.03% | 10/0 | 40/0 | 190/190 | 190/180 | 190/190 |

3. The product according to the invention of the Example 1 and a product of the prior art, that is sodium cocoyl-isethionate containing 66% of surfactant and about 28% of free fatty acid (comparison), are tested for whipped foam in water having 15 German degrees of hardness (15° dH), 37° C. and pH 7 at a product concentration of 1 g/l in each case. The foam values (foam volume) in ml at the start (that is immediately after terminating the whipping operation) and after 5 minutes are summarized in Table 3 below:

TABLE 3

| Whipped foam, pH 7, 15° dH, 1 g of substance/l, 37° C.: initial foam volume and foam volume after 5 minutes, in ml | |
|---|---|
| Comparison | Example 1 |
| 50/20 | 140/100 |

I claim:

1. A process for the preparation of acyloxyalkane-sulfonates having improved properties by esterification of fatty acids with hydroxyalkanesulfonates, which comprises esterifying at least one fatty acid of the formula 1 RCOOH (1), in which R is a branched hydrocarbon radical having 5 to 31 carbon atoms, or a mixture of branched and unbranched hydrocarbon radicals each having 5 to 31 carbon atoms, the amount of unbranched radicals being at most 50% by weight, with at least one hydroxyalkanesulfonate of the formula 2 HO—$R^1$—$SO_3$X (2), in which $R^1$ is a $C_2$ to $C_4$-alkylene or a divalent di-$C_2$ to $C_4$-alkyl ether radical and X is an alkali metal or ammonium, in the presence of an esterification catalyst and essentially in the absence of a consistency regulator at a temperature of 180° to 250° C. with removal of the water present, a product having a high content of acyloxyalkane-sulfonate being obtained.

2. The process as claimed in claim 1, wherein R is a branched radical of the formula 1a below

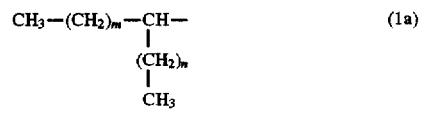

in which m is an integer from 4 to 18 and n is 0 or an integer from 1 to 10.

3. The process as claimed in claim 2, wherein R is a branched radical of the formula 1a. m is an integer from 4 to 14 and n is 0 or an integer from 1 to 6.

4. The process as claimed in claim 1, wherein $R^1$ is —$CH_2CH_2$—, —$(CH_2)_3$—, —$CH_2CH$ ($CH_3$)— or —$CH_2CH_2OCH_2CH_2$— amd X is $NH_4$ or an alkali metal.

5. The process as claimed in claim 1, wherein the esterification is carried out at a temperature of 200° to 240° C.

6. The process as claimed in claim 1, wherein the fatty acid and the hydroxyalkane-sulfonate are used in a molar ratio of 1:1 to 2:1.

7. The process as claimed in claim 1 wherein the fatty acid and the hydroxyalkane-sulfonate are used in a molar ratio of about 1:1.

8. The process as claimed in claim 1, wherein the esterification catalyst used is zinc oxide in an amount of 0.05 to 2% by weight, based on fatty acid and hydroxyalkanesulfonate.

9. The process as claimed in claim 1, wherein at least one fatty acid of the formula 1, in which R is a branched radical of the formula 1a below

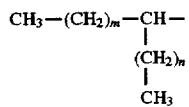

in which m is an integer from 4 to 18 and n is 0 or an integer from 1 to 10, is esterified with at least one hydroxyalkanesulfonate of the formula 2, in which $R^1$ is —$CH_2CH_2$—, —$(CH_2)_3$—, —$CH_2CH(CH_3)$— or —$CH_2CH_2OCH_2CH_2$— and X is $NH_4$ or an alkali metal, in a molar ratio of 1:1 to 2:1 in the presence of zinc oxide in an amount of 0.05 to 1% by weight, based on fatty acid and hydroxyalkanesulfonate, at a temperature of 200° to 240° C.

* * * * *